(12) United States Patent
Benni

(10) Patent No.: US 6,456,862 B2
(45) Date of Patent: Sep. 24, 2002

(54) METHOD FOR NON-INVASIVE SPECTROPHOTOMETRIC BLOOD OXYGENATION MONITORING

(75) Inventor: Paul B. Benni, Middletown, CT (US)

(73) Assignee: CAS Medical Systems, Inc., Branford, CT (US)

( * ) Notice: Subject to any disclaimer, the term of this patent is extended or adjusted under 35 U.S.C. 154(b) by 0 days.

(21) Appl. No.: 09/845,146

(22) Filed: Apr. 30, 2001

Related U.S. Application Data

(60) Provisional application No. 60/201,359, filed on May 2, 2000.

(51) Int. Cl.$^7$ ................................................ A61B 5/00
(52) U.S. Cl. ...................... 600/331; 600/323; 250/341.5
(58) Field of Search ................................ 600/323, 331, 600/336; 250/339.09, 341.1, 341.5; 356/41, 319

(56) References Cited

U.S. PATENT DOCUMENTS

| | | |
|---|---|---|
| 4,105,021 A | 8/1978 | Williams et al. |
| 4,206,764 A | 6/1980 | Williams |
| 4,223,680 A | 9/1980 | Jobsis |
| 4,281,645 A | 8/1981 | Jobsis |
| 4,321,830 A | 3/1982 | Jobsis et al. |
| 4,380,240 A | 4/1983 | Jobsis et al. |
| 4,510,838 A | 4/1985 | Jobsis et al. |
| 4,621,643 A | 11/1986 | New, Jr. et al. |
| 4,690,492 A | 9/1987 | Beard |
| 4,700,708 A | 10/1987 | New, Jr. et al. |
| 4,770,179 A | 9/1988 | New, Jr. et al. |
| 4,805,623 A * | 2/1989 | Jobsis ........................ 600/328 |
| 4,848,901 A | 7/1989 | Hood, Jr. |
| 4,865,038 A | 9/1989 | Rich et al. |
| 4,907,876 A | 3/1990 | Suzuki et al. |
| 4,913,150 A | 4/1990 | Cheung et al. |
| 4,942,877 A | 7/1990 | Sakai et al. |
| 5,054,488 A | 10/1991 | Muz |
| 5,058,588 A | 10/1991 | Kaestle |
| 5,080,098 A | 1/1992 | Willert et al. |
| 5,217,013 A | 6/1993 | Lewis et al. |
| 5,353,791 A | 10/1994 | Tamura et al. |
| 5,421,329 A | 6/1995 | Casclani et al. |
| 5,465,714 A | 11/1995 | Scheuing |
| 5,482,034 A | 1/1996 | Lewis et al. |
| 5,520,177 A | 5/1996 | Ogawa et al. |
| 5,584,296 A | 12/1996 | Cui et al. |
| 5,632,273 A | 5/1997 | Suzuki |
| 5,661,302 A | 8/1997 | Evans et al. |
| 5,697,367 A | 12/1997 | Lewis et al. |
| 5,729,333 A * | 3/1998 | Osten et al. ................... 356/39 |

(List continued on next page.)

Primary Examiner—Eric F. Winakur
(74) Attorney, Agent, or Firm—McCormick, Paulding & Huber LLP

(57) ABSTRACT

A method and apparatus for non-invasively determining the blood oxygen saturation level within a subject's tissue is provided that utilizes a near infrared spectrophotometric (NIRS) sensor capable of transmitting a light signal into the tissue of a subject and sensing the light signal once it has passed through the tissue via transmittance or reflectance. The method includes the step of determining attenuation of the light signal as the sum of: (i) attenuation attributable to deoxyhemoglobin; (ii) attenuation attributable to oxyhemoglobin; and (iii) attenuation attributable to light scattering within the subject's tissue. The present method also makes it possible to account for attenuation attributable to fixed or constant light absorbing biological tissue components, and attenuation attributable to variable characteristics of the sensor. By determining differential attenuation as a function of wavelength, the attenuation attributable to tissue light scattering characteristics, fixed light absorbing components, and measuring apparatus characteristics are mathematically cancelled out or minimized relative to the attenuation attributable to deoxyhemoglobin, and attenuation attributable to oxyhemoglobin.

44 Claims, 2 Drawing Sheets

U.S. PATENT DOCUMENTS

| | | |
|---|---|---|
| 5,752,914 A | 5/1998 | Delonnzor et al. |
| 5,758,644 A | 6/1998 | Diab et al. |
| 5,770,454 A | 6/1998 | Essenpreis et al. |
| 5,782,755 A | 7/1998 | Chance et al. |
| 5,795,292 A | 8/1998 | Lewis et al. |
| 5,879,294 A | 3/1999 | Anderson et al. |
| 5,902,235 A | 5/1999 | Lewis et al. |
| 6,192,260 B1 * | 2/2001 | Chance ...................... 600/310 |

* cited by examiner

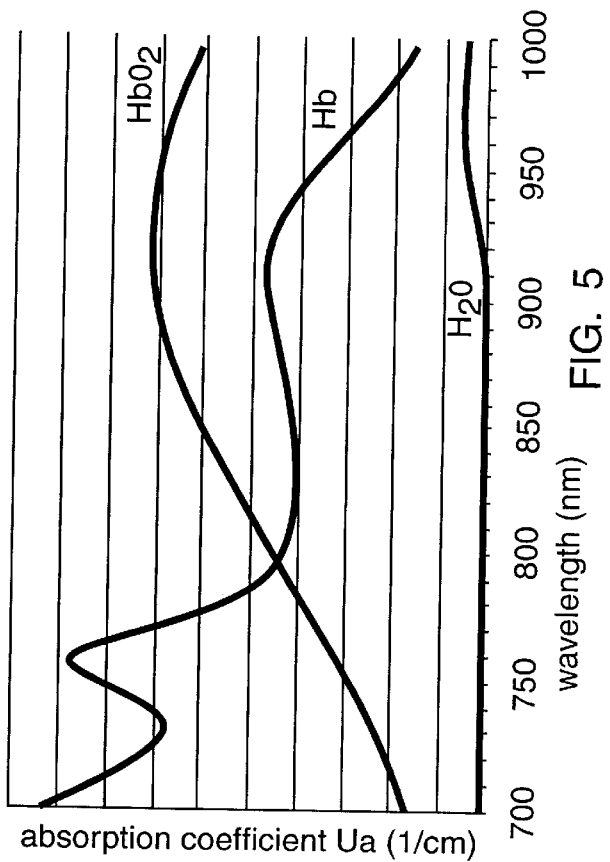
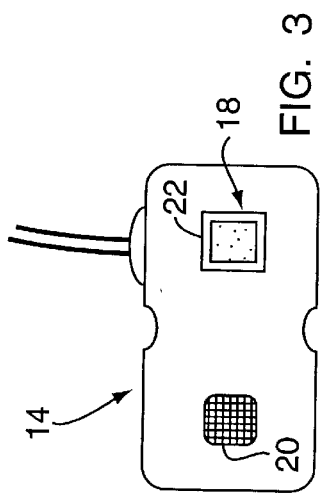
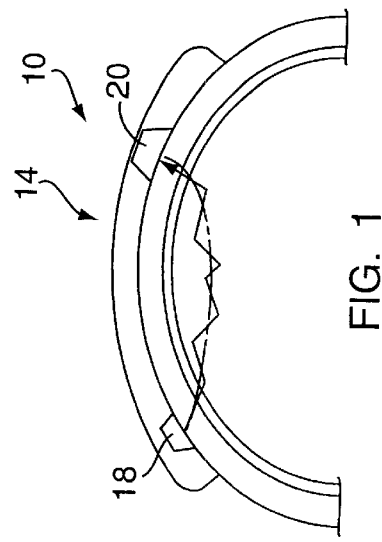
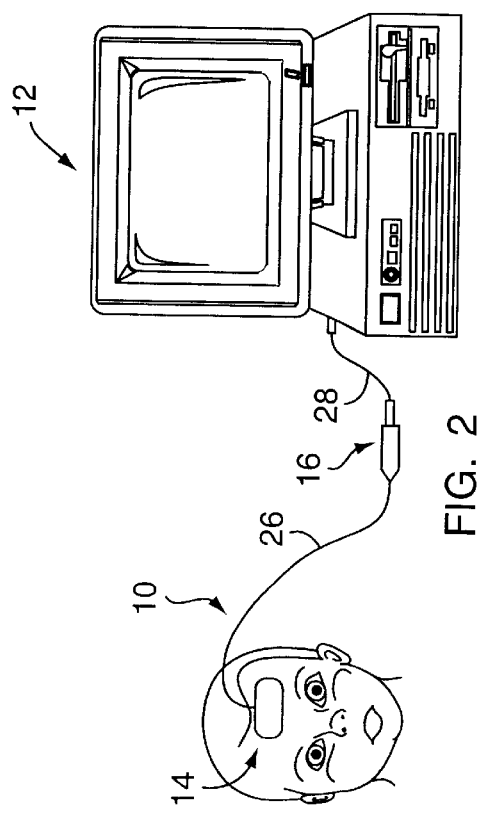
FIG. 5
FIG. 3
FIG. 1
FIG. 2

METHOD FOR NON-INVASIVE SPECTROPHOTOMETRIC BLOOD OXYGENATION MONITORING

This application claims the benefit of the filing date of U.S. Provisional Application Ser. No. 60/201,359, filed May 2, 2000.

This invention was made with Government support under Contract No. 1R43NS39723-01 awarded by the Department of Health & Human Services. The Government has certain rights in the invention.

BACKGROUND OF THE INVENTION

1. Technical Field

This invention relates to methods for non-invasively determining biological tissue oxygenation in general, and to non-invasive methods utilizing near-infrared spectroscopy (NIRS) techniques in particular.

2. Background Information

The molecule that carries the oxygen in the blood is hemoglobin. Oxygenated hemoglobin is called oxyhemoglobin ($HbO_2$) and deoxygenated hemoglobin is deoxyhemoglobin (Hb). Total hemoglobin is the summation of the two states of hemoglobin (Total Hb=$HbO_2$+Hb), and is proportional to relative blood volume changes, provided that the hematocrit or hemoglobin concentration of the blood is unchanged. The mammalian cardiovascular system consists of a blood pumping mechanism (the heart), a blood transportation system (blood vessels), and a blood oxygenation system (the lungs). Blood oxygenated by the lungs passes through the heart and is pumped into the arterial vascular system. Under normal conditions, oxygenated arterial blood consists predominately of $HbO_2$. Large arterial blood vessels branch off into smaller branches called arterioles, which profuse throughout biological tissue. The arterioles branch off into capillaries, the smallest blood vessels. In the capillaries, oxygen carried by hemoglobin is transported to the cells in the tissue, resulting in the release of oxygen molecules ($HbO_2 \rightarrow Hb$). Under normal conditions, only a fraction of the $HbO_2$ molecules give up oxygen to the tissue, depending on the cellular metabolic need. The capillaries then combine together into venuoles, the beginning of the venous circulatory system. Venuoles then combine into larger blood vessels called veins. The veins further combine and return to the heart, and then venous blood is pumped to the lungs. In the lungs, deoxygenated hemoglobin Hb collects oxygen becoming $HbO_2$ again and the circulatory process is repeated.

Oxygen saturation is defined as:

$$O_2 \text{ saturation \%} = \frac{HbO_2}{(HbO_2 + Hb)} \times 100\% \quad (Eqn. 1)$$

In the arterial circulatory system under normal conditions, there is a high proportion of $HbO_2$ to Hb, resulting in an arterial oxygen saturation (defined as $SaO_2$ %) of 95–100%. After delivery of oxygen to tissue via the capillaries, the proportion of $HbO_2$ to Hb decreases. Therefore, the measured oxygen saturation of venous blood (defined as $SvO_2$ %) is lower and may be about 70%.

One spectrophotometric method, called pulse oximetry, determines arterial oxygen saturation ($SaO_2$) of peripheral tissue (i.e. finger, ear, nose) by monitoring pulsatile optical attenuation changes of detected light induced by pulsatile arterial blood volume changes in the arteriolar vascular system. The method of pulse oximetry requires pulsatile blood volume changes in order to make a measurement. Since venous blood is not pulsatile, pulse oximetry cannot provide any information about venous blood.

Near-infrared spectroscopy (NIRS) is an optical spectrophotometric method of continually monitoring tissue oxygenation that does not require pulsatile blood volume to calculate parameters of clinical value. The NIRS method is based on the principle that light in the near-infrared range (700 to 1,000 nm) can pass easily through skin, bone and other tissues where it encounters hemoglobin located mainly within micro-circulation passages; e.g., capillaries, arterioles, and venuoles. Hemoglobin exposed to light in the near infra-red range has specific absorption spectra that varies depending on its oxidation state; i.e., oxyhemoglobin ($HbO_2$) and deoxyhemoglobin (Hb) each act as a distinct chromophore. By using light sources that transmit near-infrared light at specific different wavelengths, and measuring changes in transmitted or reflected light attenuation, concentration changes of the oxyhemoglobin ($HbO_2$) and deoxyhemoglobin (Hb) can be monitored. The ability to continually monitor cerebral oxygenation levels is particularly valuable for those patients subject to a condition in which oxygenation levels in the brain may be compromised, leading to brain damage or death.

The apparatus used in NIRS analysis typically includes a plurality of light sources, one or more light detectors for detecting reflected or transmitted light, and a processor for processing signals that represent the light emanating from the light source and the light detected by the light detector. Light sources such as light emitting diodes (LEDs) or laser diodes that produce light emissions in the wavelength range of 700–1000 nm at an intensity below that which would damage the biological tissue being examined are typically used. A photodiode or other light source detector is used to detect light reflected from or passed through the tissue being examined. The processor takes the signals from the light sources and the light detector and analyzes those signals in terms of their intensity and wave properties.

It is known that relative changes of the concentrations of $HbO_2$ and Hb can be evaluated using apparatus similar to that described above, including a processor programmed to utilize a variant of the Beer-Lambert Law, which accounts for optical attenuation in a highly scattering medium like biological tissue. The modified Beer-Lambert Law can be expressed as:

$$A_\lambda = -\log(I/I_o)_\lambda = \alpha_\lambda * C * d * B_\lambda + G \quad (Eqn.2)$$

wherein "$A_\lambda$" represents the optical attenuation in tissue at a particular wavelength $\lambda$ (units: optical density or OD); "$I_o$" represents the incident light intensity (units: $W/cm^2$); "I" represents the detected light intensity; "$\alpha_\lambda$" represents the wavelength dependent absorption coefficient of the chromophore (units: OD * $cm^{-1}$ * $\mu M^{-1}$); "C" represents the concentration of chromophore (units: $\mu M$); "d" represents the light source to detector (optode) separation distance (units: cm); "$B_\lambda$" represents the wavelength dependent light scattering differential pathlength factor (unitless); and "G" represents light attenuation due to scattering within tissue (units: OD).

Absolute measurement of chromophore concentration (C) is very difficult because G is unknown or difficult to ascertain. However, over a reasonable measuring period of several hours to days, G can be considered to remain constant, thereby allowing for the measurement of relative changes of chromophore from a zero reference baseline. Thus, if time $t_1$ marks the start of an optical measurement (i.e., a base line)

and time $t_2$ is an arbitrary point in time after $t_1$, a change in attenuation ($\Delta A$) between $t_1$ and $t_2$ can be calculated, and variables G and $I_o$ will cancel out providing that they remain constant.

The change in chromophore concentration ($\Delta C = C(t_2)-C(t_1)$) can be determined from the change in attenuation $\Delta A$, for example using the following equation derived from the Beer-Lambert Law:

$$\Delta A = -\log(I_{t2}/I_{t1})_\lambda = \alpha_\lambda * \Delta C * d * B_\lambda \qquad (Eqn.3)$$

Presently known NIRS algorithms that are designed to calculate the relative change in concentration of more than one chromophore use a multivariate form of Equation 2 or 3. To distinguish between, and to compute relative changes in, oxyhemoglobin ($\Delta HbO_2$) and deoxyhemoglobin ($\Delta Hb$), a minimum of two different wavelengths are typically used. The concentration of the $HbO_2$ and Hb within the examined tissue is determined in $\lambda$moles per liter of tissue ($\mu M$).

The above-described NIRS approach to determining oxygen saturation levels is useful, but it is limited in that it only provides information regarding a change in the level of blood oxygen saturation within the tissue. It does not provide a means for determining the total level of blood oxygen saturation within the biological tissue.

At present, information regarding the relative contributions of venous and arterial blood within tissue examined by NIRS is either arbitrarily chosen or is determined by invasive sampling of the blood as a process independent from the NIRS examination. For example, It has been estimated that NIRS examined brain tissue consists of blood comprising from about 60 to 80% venous to about 20 to 40% arterial blood. Blood samples from catheters placed in venous drainage sites such as the internal jugular vein, jugular bulb, or sagittal sinus-have been used to evaluate NIRS measurements. It has been estimated in animal studies that NIRS interrogated tissue consists of a mixed vascular bed with a venous-to-arterial ratio of about 2:1 as determined from multiple linear regression analysis of sagittal sinus oxygen saturation ($SSSO_2$) and carotid artery oxygen saturation ($SaO_2$) in comparison to NIRS measured $\Delta Hb$ and $\Delta HbO_2$. An expression representing the mixed venous/arterial oxygen saturation ($SmvO_2$) in NIRS examined tissue is shown by the equation:

$$SmvO_2 = Kv*SvO_2 + Ka*SaO_2 \qquad (Eqn.4)$$

where "$SvO_2$" represents venous oxygen saturation; "$SaO_2$" represents arterial oxygen saturation; and Kv and Ka are the weighted venous and arterial contributions respectively, with Kv+Ka=1. The parameters Kv and Ka may have constant values, or they may be a function of $SvO_2$ and $SaO_2$. Determined oxygen saturation from the internal jugular vein ($SijvO_2$), jugular bulb ($SjbO_2$), or sagittal sinus ($SssO_2$) can be used to represent $SvO_2$. Therefore, the value of each term in Equation 4 is empirically determined, typically by discretely sampling or continuously monitoring and subsequently evaluating patient arterial and venous blood from tissue that the NIRS sensor is examining, and using regression analysis to determine the relative contributions of venous and arterial blood independent of the NIRS examination.

What is needed, therefore, is a method for non-invasively determining the level of oxygen saturation within biological tissue that can determine the total oxygen saturation level rather than a change in level; a method that provides calibration means to account for light attenuation due to scattering within tissue (G); and a method that can non-invasively distinguish the contribution of oxygen saturation attributable to venous blood and that which is attributable to arterial blood.

DISCLOSURE OF THE INVENTION

It is, therefore, an object of the present invention to provide a method for non-invasively determining the total level of blood oxygen saturation within biological tissue.

It is a further object of the present invention to provide a method that provides calibration means to account for light attenuation due to scattering within tissue, light attenuation due to fixed tissue absorbers, and light attenuation due to variability between light measuring apparatuses.

It is a still further object of the present invention to provide a method that can non-invasively distinguish between the contribution of oxygen saturation attributable to venous blood and that attributable to arterial blood.

According to the present invention, a method and apparatus for non-invasively determining the blood oxygen saturation level within a subject's tissue is provided that utilizes a near infrared spectrophotometric (NIRS) sensor capable of transmitting a light signal into the tissue of a subject and sensing the light signal once it has passed through the tissue via transmittance or reflectance. The method includes the step of determining attenuation of the light signal as the sum of: (i) attenuation attributable to deoxyhemoglobin; (ii) attenuation attributable to oxyhemoglobin; and (iii) attenuation attributable to light scattering within the subject's tissue. The present method also makes it possible to account for attenuation attributable to fixed or constant light absorbing biological tissue components, and attenuation attributable to variable characteristics of the sensor. By determining differential attenuation as a function of wavelength, the attenuation attributable to tissue light scattering characteristics, fixed light absorbing components, and measuring apparatus characteristics are mathematically cancelled out or minimized relative to the attenuation attributable to deoxyhemoglobin, and attenuation attributable to oxyhemoglobin.

In order to account for the resulting minimized differential attenuation attributable to tissue light scattering characteristics, fixed light absorbing components, and measuring apparatus characteristics, each of the parameters must be measured or calibrated out. Since direct measurement is difficult, calibration to empirically determined data combined with data developed using the NIRS sensor is performed by using regression techniques. The empirically determined data is collected at or about the same time the data is developed with the NIRS sensor. Once the calibration parameters associated with attenuation attributable to tissue light scattering characteristics, fixed light absorbing components, and measuring apparatus characteristics have been determined, the NIRS sensor can be calibrated.

The calibrated sensor can then be used to accurately and non-invasively determine the total oxygen saturation level in the original subject tissue or other subject tissue. In addition, if the separation distance ("d") between the light source to the light detector is known or is determinable, and if the value of "B", which represents the wavelength dependent light scattering differential pathlength factor, is known, then the total amount of concentrations of deoxyhemoglobin (Hb) and oxyhemoglobin ($HbO_2$) within the examined tissue can be determined using the present method and apparatus.

The calibrated sensor can be used subsequently to calibrate similar sensors without having to invasively produce a blood sample. Hence, the present method and apparatus enables a non-invasive determination of the blood oxygen saturation level within tissue. For example, an operator can create reference values by sensing a light signal or other reference medium using the calibrated sensor. The operator can then calibrate an uncalibrated sensor by sensing the same light signal or reference medium, and subsequently adjusting the uncalibrated sensor into agreement with the calibrated sensor. Hence, once a reference sensor is created, other similar sensors can be calibrated without the need for invasive procedure.

There are, therefore, several advantages provided by the present method and apparatus. Those advantages include: 1) a practical non-invasive method and apparatus for determining oxygen saturation within tissue that can be used to determine the total blood oxygen saturation within tissue as opposed to a change in blood oxygen saturation; 2) a calibration method that accounts for light attenuation due to scattering within tissue (G), fixed tissue absorbers (F), and measuring apparatus variability (N); and 3) a practical non-invasive method and apparatus for determining oxygen saturation within tissue that can distinguish between the contribution of oxygen saturation attributable to venous blood and that saturation attributable to arterial blood.

In an alternative embodiment, aspects of the above-described methodology are combined with pulse oximetry techniques to provide a non-invasive method of distinguishing between blood oxygen saturation within tissue that is attributable to venous blood and that which is attributable to arterial blood. Pulse oximetry is used to determine arterial oxygen saturation, and the arterial oxygen saturation is, in turn, used to determine the venous oxygen saturation.

These and other objects, features, and advantages of the present invention method and apparatus will become apparent in light of the detailed description of the invention provided below and the accompanying drawings. The methodology and apparatus described below constitute a preferred embodiment of the underlying invention and do not, therefore, constitute all aspects of the invention that will or may become apparent by one of skill in the art after consideration of the invention disclosed overall herein.

BRIEF DESCRIPTION OF THE DRAWINGS

FIG. 1 is a diagrammatic representation of a NIRS sensor placed on a subject's head.

FIG. 2 is a diagrammatic representation of a NIRS sensor.

FIG. 3 is a diagrammatic view of a NIRS sensor.

FIG. 5 is a graph showing an exemplary plot of absorption coefficient vs. wavelength.

DETAILED DESCRIPTION THE INVENTION

Figure 4:
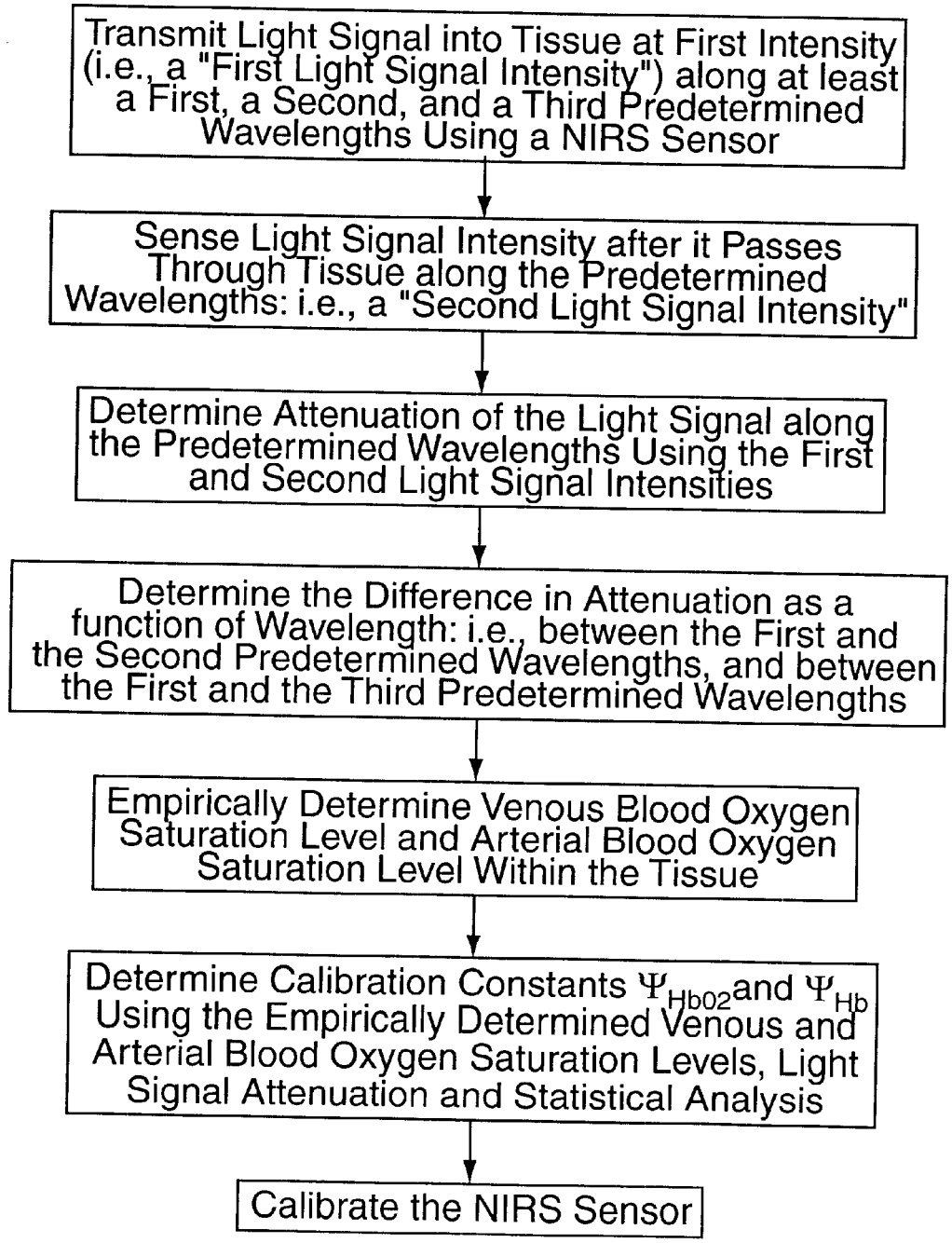
FIG. 4 is a block diagram of the present methodology for calibrating a NIRS sensor.

The present method of and apparatus for non-invasively determining the blood oxygen saturation level within a subject's tissue is provided that utilizes a near infrared spectrophotometric (NIRS) sensor that includes a transducer capable of transmitting a light signal into the tissue of a subject and sensing the light signal once it has passed through the tissue via transmittance or reflectance. The present method and apparatus can be used with a variety of NIRS sensors. The NIRS sensor described below, which is the subject of co-pending U.S. patent application Ser. No. 09/434,146 filed Nov. 4, 1999 commonly assigned with the present application, discloses a preferred NIRS sensor. The present method is not limited to use with this preferred NIRS sensor, however.

Referring to FIGS. 1–5, the preferred NIRS sensor includes a transducer portion 10 and processor portion 12. The transducer portion 10 includes an assembly housing 14 and a connector housing 16. The assembly housing 14, which is a flexible structure that can be attached directly to a subject's body, includes one or more light sources 18 and a light detector 20. A disposable adhesive envelope or pad is used for mounting the assembly housing 14 easily and securely to the subject's skin. Light signals of known but different wavelengths from the light sources 18 emit through a prism assembly 22. The light sources 18 are preferably laser diodes that emit light at a narrow spectral bandwidth at predetermined wavelengths. In one embodiment, the laser diodes are mounted within the connector housing 16. The laser diodes are optically interfaced with a fiber optic light guide to the prism assembly 22 that is disposed within the assembly housing 14. In a second embodiment, the light sources 18 are mounted within the assembly housing 14. A first connector cable 26 connects the assembly housing 14 to the connector housing 16 and a second connector cable 28 connects the connector housing 16 to the processor portion 12. The light detector 20 includes one or more photodiodes. The photodiodes are also operably connected to the processor portion 12 via the first and second connector cables 26,28. The processor portion 12 includes a processor for processing light intensity signals from the light sources 18 and the light detector 20.

The processor utilizes an algorithm that characterizes a change in attenuation as a function of the difference in attenuation between different wavelengths. The present method advantageously accounts for but minimizes the attenuation effects of the scattering variable "G", pathlength $B^*d$, and the absorption "F" due to other components present in biological tissue (i.e. bone, water, skin pigmentation, etc.) that have a relatively flat or very low absorption spectra over the measured wavelength range. In addition, the present method accounts for any offset attenuation "N" due to the characteristics of the sensor that may or may not be wavelength independent. The present method algorithm can be expressed as:

$$A_{\lambda 1} - A_{\lambda 2} = \Delta A_{\lambda 1 - \lambda 2} = \Delta A_{\lambda 12} \quad \text{(Eqn.5)}$$

where $A_{\lambda 1}$ and $A_{\lambda 2}$ are in the form of Equation 6 below which is a modified version of Equation 2 that accounts for attenuation due to "F" and "N":

$$A_\lambda = -\log(I/I_o)_\lambda = \alpha_\lambda {}^* C^* d^* B_\lambda + G + F + N \quad \text{(Eqn.6)}$$

Substituting Equation 6 into Equation 5 for $A_{\lambda 1}$ and $A_{\lambda 2}$, the terms "F" and "N" within Equation 5 are subtracted out, provided they represent constant light absorption over the measurement wavelengths and provided the same sensor is used to sense the light signal at the various wavelengths. Therefore, in the case where the differential pathlength factor B is wavelength independent, then $\Delta A_{\lambda 12}$ can be expressed as:

$$\Delta A_{\lambda 12} = \log[(I_{\lambda 2}/I o_{\lambda 2})^*(I_{\lambda 1}/I o_{\lambda 1})] = \Delta \alpha_{c \lambda 12} c d B + \Delta G_{\lambda 12} \quad \text{(Eqn.7)}$$

and rewritten in expanded form:

$$\Delta A_{\lambda12}=(\alpha_{Hb\lambda1}-\alpha_{Hb\lambda2})[Hb]dB+(\alpha_{HbO_2\lambda1}-\alpha_{HbO_2\lambda2})[HbO_2]dB+\Delta G_{\lambda12} \quad (\text{Eqn.8})$$

Alternatively, the differential pathlength factor "B" may be wavelength dependent. In this case, it is desirable to separate $B_\lambda$ into two components:

$$B_\lambda = B * k_{80} \quad (\text{Eqn.9})$$

The parameter B is determined at one specific wavelength and the parameter $k_\lambda$ represents how B would change at other wavelengths. To continue with the mathematical derivations, it is then desirable to combine the pathlength wavelength dependent parameter $k_\lambda$ to $\alpha_\lambda$:

$$\alpha'_\lambda = \alpha_\lambda * k_\lambda \quad (\text{Eqn.10})$$

The parameter $\alpha'_\lambda$ represents the absorption coefficient $\alpha_\lambda$ adjusted by pathlength wavelength dependent parameter $k_\lambda$. Incorporation of these modifications into Equation 7 results in the following:

$$\Delta A_{\lambda12}=(\alpha'_{Hb\lambda1}-\alpha'_{Hb\lambda2})[Hb]dB+(\alpha'_{HbO_2\lambda1}-\alpha'_{HbO_2\lambda2})[HbO_2]dB+\Delta G_{\lambda12} \quad (\text{Eqn.11})$$

where:

$$(\alpha'_{Hb\lambda1}-\alpha'_{Hb\lambda2})[Hb]dB$$

represents the attenuation attributable to Hb;

$$(\alpha'_{HbO_2\lambda1}-\alpha'_{HbO_2\lambda2})[HbO_2]dB$$

represents the attenuation attributable to $HbO_2$; and $$\Delta G_{\lambda12}$$

represents the attenuation attributable to light scattering within tissue (G).

In another alternative case, the light absorption due to the fixed tissue absorbers (F), and sensor variability (N) may not be constant over the measuring wavelengths. In this case, differential attenuation as a function of wavelength would result in the parameters $\Delta F_{\lambda12}$ and $\Delta N_{\lambda12}$, to be included in Equation 7 or Equation 11.

$$\Delta A_{\lambda12}=(\alpha'_{Hb\lambda1}-\alpha'_{Hb\lambda2})[Hb]dB+(\alpha'_{HbO_2\lambda1}-\alpha'_{HbO_2\lambda2})[HbO_2]dB+\Delta G_{\lambda12}+\Delta F_{\lambda12}+\Delta N_{\lambda12} \quad (\text{Eqn.12})$$

The parameter $\Delta N_{\lambda12}$, does not change in magnitude for a particular NIRS sensor. The parameter $\Delta F_{\lambda12}$, by definition, would be the result of differential attenuation due to components that have a relatively flat or very low absorption spectra over the measured wavelength range, and therefore would be a very small and relatively constant value when compared to the differential attenuation due to hemoglobin. Thus, $\Delta F_{\lambda12}$ can be seen as a fixed absorber error correcting parameter in Equation 12. Therefore, these parameters then can be summed together by superposition to become $\Delta G'_{\lambda12}$:

$$\Delta G'_{\lambda12}=\Delta G_{\lambda12}+\Delta F_{\lambda12}+\Delta N_{\lambda12} \quad (\text{Eqn.13})$$

Incorporation of these modifications into Equation 12 results in the following:

$$\Delta A_{\lambda12}=(\alpha'_{Hb\lambda1}-\alpha'_{Hb\lambda2})[Hb]dB+(\alpha'_{HbO_2\lambda1}-\alpha'_{HbO_2\lambda2})[HbO_2]dB+\Delta G'_{\lambda12} \quad (\text{Eqn.14})$$

Note that if $\Delta G_{\lambda12} << G_{\lambda1}$ and $G_{\lambda2}$, the effect of G is minimized within Equation 11, in contrast with the effect of G within Equation 2, at the cost of utilizing one more wavelength to determine Hb and $HbO_2$. Thus, a minimum of three different wavelengths is needed to determine Hb and $HbO_2$. Also in the alternative case, $\Delta G_{\lambda12}$ minimizes the effects of light attenuation due to scattering within tissue (G), fixed tissue absorbers (F), and sensor variability (N), at the same cost of utilizing one more wavelength.

The multivariate form of Equation 11 or 14, after mathematical manipulation, is used to determine $HbO_2$ and Hb with three different wavelengths:

$$\begin{bmatrix}\Delta A_{\lambda12}-\Delta G'_{\lambda12}\\ \Delta A_{\lambda13}-\Delta G'_{\lambda13}\end{bmatrix}(dB)^{-1}=\begin{bmatrix}\Delta\alpha'_{Hb\lambda12}\Delta\alpha'_{HbO_2\lambda12}\\ \Delta\alpha'_{Hb\lambda13}\Delta\alpha'_{HbO_2\lambda13}\end{bmatrix}\begin{bmatrix}Hb\\ HbO_2\end{bmatrix} \quad (\text{Eqn.15})$$

Rearranging and solving for $HbO_2$ and Hb, simplifying the $\Delta\alpha'$ matrix into $[\Delta\alpha']$:

$$\begin{bmatrix}\Delta A_{\lambda12}\\ \Delta A_{\lambda13}\end{bmatrix}[\Delta\alpha']^{-1}(dB)^{-1}-\begin{bmatrix}\Delta G'_{\lambda12}\\ \Delta G'_{\lambda13}\end{bmatrix}[\Delta\alpha']^{-1}(dB_\lambda)^{-1}=\begin{bmatrix}Hb\\ HbO_2\end{bmatrix} \quad (\text{Eqn.16})$$

and rewritten into:

$$\begin{bmatrix}A_{Hb}\\ A_{HbO_2}\end{bmatrix}(dB)^{-1}-\begin{bmatrix}\Psi_{Hb}\\ \Psi_{HbO_2}\end{bmatrix}(dB)^{-1}=\begin{bmatrix}Hb\\ HbO_2\end{bmatrix} \quad (\text{Eqn.17})$$

The parameters $A_{Hb}$ and $A_{HbO2}$ represent the product of the matrices $[\Delta A_\lambda]$ and $[\Delta\alpha']^{-1}$ and the parameters $\Psi_{Hb}$ and $\Psi_{HbO2}$ represent the product of the matrices $[\Delta G'_\lambda]$ and $[\Delta\alpha']^{-1}$. To determine the level of cerebral blood oxygen saturation ($CrSO_2$), Equation 17 is rearranged using the form of Equation 1 and is expressed as follows:

$$CrSO_2\% = \frac{(A_{HbO_2}-\Psi_{HbO_2})}{(A_{HbO_2}-\Psi_{HbO_2}+A_{Hb}-\Psi_{Hb})}*100\% \quad (\text{Eqn.18})$$

Note that the pathlength d*B cancels out in the manipulation from Equation 17 to Equation 18.

The value for $CrSO_2$ is initially determined from $SmvO_2$ using Equation 4 and the empirically determined values for $SvO_2$ and $SaO_2$. The empirically determined values for $SvO_2$ and $SaO_2$ are based on data developed by discrete sampling or continuous monitoring of the subject's blood performed at or about the same time as the sensing of the tissue with the sensor. The temporal proximity of the NIRS sensing and the development of the empirical data helps assure accuracy. The initial values for Kv and Ka within Equation 4 are clinically reasonable values for the circumstances at hand. The values for $A_{HbO2}$ and $A_{Hb}$ are determined mathematically using the values for $Io_\lambda$ and $I_\lambda$ for each wavelength sensed with the NIRS sensor (e.g., using Equation 2 or 6). The calibration parameters $\Psi_{Hb}$ and $\Psi_{HbO2}$, which account for the effects of light attenuation due to scattering within tissue (G), fixed tissue absorbers (F), and measuring apparatus variability (N), are then determined using Equation 18 and non-linear regression techniques by correlation to different weighted values of $SvO_2$ and $SaO_2$; i.e., different values of Ka and Kv. Statistically acceptable values of Kv and Ka and $\Psi_{Hb}$ and $\Psi_{HbO2}$ are converged upon using the non-linear regression techniques. Experimental findings show that after proper selection of Ka and Kv, the calibration parameters $\Psi_{Hb}$ and $\Psi_{HbO2}$ are constant within a statistically acceptable margin of error for an individual NIRS sensor used to monitor brain oxygenation on different human subjects. In other words, once the sensor is calibrated it can be used on various human subjects and produce accurate information for each human subject.

In the determination of the $CrSO_2$ percentage, the photon pathlength "d*B" cancels out. If, however, the photon pathlength is known or estimated, then the determination of the total value of Hb and/or $HbO_2$ is possible. For example, if a value for pathlength "d*B" is input into Equation 17 along with the calibration values $\Psi_{Hb}$ and $\Psi_{HbO2}$, then the total value of Hb and/or $HbO_2$ can be calculated. The light source to detector separation (optode) distance parameter "d" in the pathlength calculation is a measurable value and can be made constant by setting a fixed distance between light source to detector in the NIRS sensor design. Alternatively, the parameter "d" can be measured once the optodes are placed on the subject by use of calipers, ruler, or other distance measurement means. The pathlength differential factor "B" is more difficult to measure and requires more sophisticated equipment. From a large data set of measured neonatal and adult head differential pathlength factor values, an estimation of the value of "B" can be determined within a statistically acceptable margin of error. Substitution of these predetermined values of "B" into Equation 17 results in the determination of the total values of Hb and $HbO_2$.

An alternative method of determining total values of Hb and $HbO_2$ combines Equation 3 and Equation 17 together. The multivariate form of Equation 3 is shown below:

$$\begin{bmatrix} -\log(I_{t2}/I_{t1})_{\lambda 1}/(d*B_{\lambda 1}) \\ -\log(I_{t2}/I_{t1})_{\lambda 2}/(d*B_{\lambda 2}) \\ -\log(I_{t2}/I_{t1})_{\lambda 3}/(d*B_{\lambda 3}) \end{bmatrix} = \begin{bmatrix} \alpha_{Hb\lambda 1} & \alpha_{HbO_2\lambda 1} \\ \alpha_{Hb\lambda 2} & \alpha_{HbO_2\lambda 2} \\ \alpha_{Hb\lambda 3} & \alpha_{HbO_2\lambda 3} \end{bmatrix} * \begin{bmatrix} \Delta Hb \\ \Delta HbO_2 \end{bmatrix} \quad \text{(Eqn. 19)}$$

At time $t=t_1$, the values of $\Delta Hb$ and $\Delta HbO_2$ are zero. Applying Equation 17, and knowing the calibration values of $\Psi_{Hb}$ and $\Psi_{HbO2}$ at a predetermined differential pathlength factor "B" and optode separation "d", the total absolute values of Hb and $HbO_2$ are determined at time $t=t_1$, which are represented by $[Hb]_{t1}$ and $[HbO_2]_{t1}$ respectively. At time $t=t_2$, the values of $\Delta Hb$ and $\Delta HbO_2$ are then determined using Equation 19. The total values of Hb and $HbO_2$ are then determined at time $t=t_2$ using the following equations:

$$[Hb]_{t2} = \Delta Hb(t_2) + [Hb]_{t1} \quad \text{(Eqn.20)}$$

$$[HbO_2]_{t2} = \Delta HbO_2(t_2) + [HbO_2]_{t1} \quad \text{(Eqn.21)}$$

Equations 20 and 21 are valid only if all the shared parameters in Equations 17 and 19 are exact. Reduced to practice, the advantage of combining Equations 17 and 19 result in improved signal to noise ratio (SNR) in the calculation of the total values for Hb and $HbO_2$. Conversely, improved SNR in the calculation of $CrSO_2$ is also obtained from the following expression:

$$CrSO_2(t_2) = \frac{[HbO_2]_{t2}}{([HbO2]_{t2} + [Hb]_{t2})} * 100\% \quad \text{(Eqn. 22)}$$

After the calibration parameters $\Psi_{Hb}$ and $\Psi_{HbO2}$ are determined using the above-described methodology for an individual NIRS sensor, this particular sensor is said to be calibrated. A calibrated NIRS sensor affords accurate measurement of total tissue oxygen saturation, $CrSO_2$, by non-invasive means. The calibrated sensor can be used thereafter on any human patient, including adults and neonates. Although the present method is described above in terms of sensing blood oxygenation within cerebral tissue, the present method and apparatus are not limited to cerebral applications and can be used to determine blood oxygenation within tissue found elsewhere within the subject's body.

According to an additional aspect of the present invention, the above-described method can also be used to establish a calibrated "reference" sensor that can be used to calibrate similar sensors through the use of a phantom sample (also referred to as a "reference sample"). The phantom sample has optical characteristics that are similar to the tissue being examined by the NIRS sensor. The calibrated reference NIRS sensor is used to sense the phantom sample and produce reference values. Similar, but uncalibrated, NIRS sensors can thereafter be calibrated by sensing the same phantom sample and adjusting either the hardware of the uncalibrated sensor or the output of the uncalibrated sensor until the output of the uncalibrated sensor agrees with the reference values produced by the calibrated reference sensor. Therefore, the calibration parameters $\Psi_{Hb}$ and $\Psi_{HbO2}$ for the uncalibrated sensor would be determined from the phantom sample. This technique makes it unnecessary to calibrate each new sensor in the manner described above, and thereby provides a relatively quick and cost effective way to calibrate NIRS sensors.

Besides Hb and $HbO_2$, other biological constituents of interest (e.g., cytochrome $aa_3$, etc.) could be determined using the multivariate forms of equations 2, 3, 6 or 7. For each additional constituent to be determined, an additional measuring wavelength will be needed.

In an alternative embodiment, the above-described methodology can be combined with pulse oximetry techniques to provide an alternative non-invasive method of distinguishing between oxygen saturation attributable to venous blood and that attributable to arterial blood. As demonstrated by Equation 4, $SmvO_2$ is determined by the ratio of venous oxygen saturation $SvO_2$ and arterial oxygen saturation $SaO_2$. A calibrated NIRS sensor affords accurate measurement of total tissue oxygen saturation, $CrSO_2$, by using regression techniques by correlation to mixed venous oxygen saturation $SmvO_2$. Therefore, the following expression will result:

$$CrSO_2 = SmvO_2 = Kv*SvO_2 + Ka*SaO_2 \quad \text{(Eqn.23)}$$

Non-invasive pulse oximetry techniques can be used to determine the arterial oxygen saturation ($SaO_2$) of peripheral tissue (i.e. finger, ear, nose) by monitoring pulsatile optical attenuation changes of detected light induced by pulsatile arterial blood volume changes in the arteriolar vascular system. Arterial blood oxygen saturation determined by pulse oximetry is clinically denoted as $SpO_2$. If NIRS monitoring and pulse oximetry monitoring are done simultaneously and $SpO_2$ is set equal to $SaO_2$ in Equation 23, then venous oxygen saturation can be determined from the following expression:

$$SvO_2 = \frac{CrSO_2 - (Ka*SpO_2)}{Kv} \quad \text{(Eqn. 24)}$$

For the brain, venous oxygen saturation SvO2 would be determined from internal jugular vein (SijvO$_2$), jugular bulb (SjbO$_2$), or sagittal sinus (SssO$_2$) and the parameters Ka and Kv would be empirically determined during the calibration of the NIRS sensor. Under most physiological conditions, SpO$_2$ is representative of brain arterial oxygen saturation SaO$_2$. Therefore, depending on which venous saturation parameter was used to calibrate the NIRS sensor, this clinically important parameter (i.e., SijvO$_2$, SjbO$_2$, or SssO$_2$) can be determined by Equation 24 by non-invasive means.

Since many changes and variations of the disclosed embodiment of the invention may be made without departing from the inventive concept, it is not intended to limit the invention otherwise than as required by the appended claims.

What is claimed is:

1. A method for non-invasively determining a blood oxygen saturation level within a subject's tissue using a near infrared spectrophotometric sensor, said method comprising the steps of:

transmitting a light signal into the subject's tissue at a predetermined first intensity using the sensor, wherein the transmitted light signal includes a first wavelength, a second wavelength, and a third wavelength;

sensing a second intensity of the light signal, using the sensor, along the first, second, and third wavelengths after the light signal travels through the subject;

wherein the sensor is calibrated using empirical data that relates to the subject's tissue that is sensed by the sensor to account for light signal attenuation resulting from light signal scattering within the subject's tissue;

determining an attenuation of the light signal for each of the first, second, and third wavelengths using the predetermined first intensity and the sensed second intensity of the first, second, and third wavelengths;

determining a difference in attenuation of the light signal between the first wavelength and the second wavelength, and between the first wavelength and the third wavelength;

determining the blood oxygen saturation level within the subject's tissue using the difference in attenuation between the first wavelength and the second wavelength, and the difference in attenuation between the first wavelength and the third wavelength.

2. The method of claim 1, wherein the sensor is calibrated using equation:

$$SmvO_2 = Kv*SvO_2 + Ka*SaO_2.$$

3. The method of claim 2, wherein the sensor is calibrated by using empirical data to determine a first calibration constant and a second calibration constant.

4. The method of claim 3, wherein the step of determining the blood oxygen saturation level within the subject's tissue utilizes the equation:

$$CrSO_2 \% = \frac{(A_{HbO_2} - \Psi_{HbO_2})}{(A_{HbO_2} - \Psi_{HbO_2} + A_{Hb} - \Psi_{Hb})} * 100\%$$

where $\Psi_{HbO2}$ represents the first calibration constant, $\Psi_{Hb}$ represents the second calibration constant, $A_{HbO2}$ represents a difference in attenuation of light signal attributable to oxyhemoglobin, and $A_{Hb}$ represents a difference in attenuation of light signal attributable to deoxyhemoglobin.

5. The method of claim 4, further comprising the steps of:

determining a photon pathlength d*B; and determining a concentration of oxyhemoglobin and a concentration of deoxyhemoglobin within the subject's tissue using the first and second calibration constants.

6. The method of claim 5, wherein the concentration of oxyhemoglobin and the concentration of deoxyhemoglobin within the subject's tissue are determined using the equation:

$$\begin{bmatrix} A_{Hb} \\ A_{HbO_2} \end{bmatrix} (dB)^{-1} - \begin{bmatrix} \Psi_{Hb} \\ \Psi_{HbO_2} \end{bmatrix} (dB)^{-1} = \begin{bmatrix} Hb \\ HbO_2 \end{bmatrix}.$$

7. The method of claim 6, wherein the step of determining a difference in attenuation of the light signal between the first wavelength and the second wavelength utilizes the equation:

$$\Delta A_{\lambda 12} = \log[(I_{\lambda 2}/Io_{\lambda 2})*(I_{\lambda 1}/Io_{\lambda 1})] = \Delta\alpha_{c\lambda 12} cdB + \Delta G_{\lambda 12}$$

and the step of determining a difference in attenuation of the light signal between the first wavelength and the third wavelength utilizes the equation:

$$\Delta A_{\lambda 13} = \log[(I_{\lambda 3}/Io_{\lambda 3})*(I_{\lambda 1}/Io_{\lambda 1})] = \Delta\alpha_{c\lambda 13} cdB + \Delta G_{\lambda 13}.$$

8. The method of claim 6, wherein the step of determining a difference in attenuation of the light signal between the first wavelength and the second wavelength utilizes the equation:

$$\Delta A_{\lambda 12} = (\alpha'_{Hb\lambda 1} - \alpha'_{Hb\lambda 2})[Hb]dB + (\alpha'_{HbO_2\lambda 1} - \alpha'_{HbO_2\lambda 2})[HbO_2]dB + \Delta G_{\lambda 12}$$

and the step of determining a difference in attenuation of the light signal between the first wavelength and the third wavelength utilizes the equation:

$$\Delta A_{\lambda 13} = (\alpha'_{Hb\lambda 1} - \alpha'_{Hb\lambda 3})[Hb]dB + (\alpha'_{HbO_2\lambda 1} - \alpha'_{HbO_2\lambda 3})[HbO_2]dB + \Delta G_{\lambda 13}.$$

9. The method of claim 6, wherein the step of determining a difference in attenuation of the light signal between the first wavelength and the second wavelength utilizes the equation:

$$\Delta A_{\lambda 12} = (\alpha'_{Hb\lambda 1} - \alpha'_{Hb\lambda 2})[Hb]dB + (\alpha'_{HbO_2\lambda 1} - \alpha'_{HbO_2\lambda 2})[HbO_2]dB + \Delta G'_{\lambda 12}$$

and the step of determining a difference in attenuation of the light signal between the first wavelength and the third wavelength utilizes the equation:

$$\Delta A_{\lambda 13} = (\alpha'_{Hb\lambda 1} - \alpha'_{Hb\lambda 3})[Hb]dB + (\alpha'_{HbO_2\lambda 1} - \alpha'_{HbO_2\lambda 3})[HbO_2]dB + \Delta G'_{\lambda 13}.$$

10. The method of claim 1, wherein the step of determining a difference in attenuation of the light signal between the first wavelength and the second wavelength utilizes the equation:

$$\Delta A_{\lambda 12} = \log[(I_{\lambda 2}/Io_{\lambda 2})*(I_{\lambda 1}/Io_{\lambda 1})] = \Delta \alpha_{c\lambda 12} cdB + \Delta G_{\lambda 12}$$

and the step of determining a difference in attenuation of the light signal between the first wavelength and the third wavelength utilizes the equation:

$$\Delta A_{\lambda 13} = \log[(I_{\lambda 3}/Io_{\lambda 3})*(I_{\lambda 1}/Io_{\lambda 1})] = \Delta \alpha_{c\lambda 13} cdB + \Delta G_{\lambda 13}.$$

11. The method of claim 1, wherein the step of determining a difference in attenuation of the light signal between the first wavelength and the second wavelength utilizes the equation:

$$\Delta A_{\lambda 12} = (\alpha'_{Hb\lambda 1} - \alpha'_{Hb\lambda 2})[Hb]dB + (\alpha'_{HbO_2\lambda 1} - \alpha'_{HbO_2\lambda 2})[HbO_2]dB + \Delta G_{\lambda 12}$$

and the step of determining a difference in attenuation of the light signal between the first wavelength and the third wavelength utilizes the equation:

$$\Delta A_{\lambda 13} = (\alpha'_{Hb\lambda 1} - \alpha'_{Hb\lambda 3})[Hb]dB + (\alpha'_{HbO_2\lambda 1} - \alpha'_{HbO_2\lambda 3})[HbO_2]dB + \Delta G_{\lambda 13}.$$

12. The method of claim 1, wherein the step of determining a difference in attenuation of the light signal between the first wavelength and the second wavelength utilizes the equation:

$$\Delta A_{\lambda 12} = (\alpha'_{Hb\lambda 1} - \alpha'_{Hb\lambda 2})[Hb]dB + (\alpha'_{HbO_2\lambda 1} - \alpha'_{HbO_2\lambda 2})[HbO_2]dB + \Delta G'_{\lambda 12}$$

and the step of determining a difference in attenuation of the light signal between the first wavelength and the third wavelength utilizes the equation:

$$\Delta A_{\lambda 13} = (\alpha'_{Hb\lambda 1} - \alpha'_{Hb\lambda 3})[Hb]dB + (\alpha'_{HbO_2\lambda 1} - \alpha'_{HbO_2\lambda 3})[HbO_2]dB + \Delta G'_{\lambda 13}.$$

13. The method of claim 2, further comprising the steps of:
  determining a blood oxygen saturation level attributable to arterial blood within the subject's tissue using a pulse oximetry technique; and
  determining a blood oxygen saturation level attributable to venous blood within the subject's tissue using the equation:

$$SvO_2 = \frac{CrSO_2 - (Ka * SpO_2)}{Kv}.$$

14. A method for determining a blood oxygen saturation level within a subject's tissue using a near infrared spectrophotometric sensor attached to the skin of the subject, said method comprising the steps of:
  transmitting a light signal into the subject's tissue at a predetermined first intensity, wherein the transmitted light signal includes a first wavelength, a second wavelength, and a third wavelength;
  sensing a second intensity of the light signal along the first, second, and third wavelengths after the light signal travels through the subject;
  determining an attenuation of the light signal for each of the first, second, and third wavelengths using the predetermined first intensity and the sensed second intensity of the first, second, and third wavelengths;
  determining a difference in attenuation of the light signal between the first wavelength and the second wavelength, and between the first wavelength and the third wavelength;
  determining a first calibration constant and a second calibration constant using empirical data developed from the subject at or about the same time as when the sensing occurs;
  determining the blood oxygen saturation level within the subject's tissue using the difference in attenuation between the first wavelength and the second wavelength, and the difference in attenuation between the first wavelength and the third wavelength, and the first calibration constant and the second calibration constant.

15. The method of claim 14 wherein the empirical data is collected by discretely sampling a venous blood source and an arterial blood source from the subject.

16. The method of claim 14 wherein the empirical data is collected by continuously monitoring a venous blood source and an arterial blood source from the subject.

17. The method of claim 14, wherein the sensor is calibrated using equation:

$$SmvO_2 = Kv * SvO_2 + Ka * SaO_2.$$

18. The method of claim 17, wherein the step of determining the blood oxygen saturation level within the subject's tissue utilizes the equation:

$$CrSO_2 \% = \frac{(A_{HbO_2} - \Psi_{HbO_2})}{(A_{HbO_2} - \Psi_{HbO_2} + A_{Hb} - \Psi_{Hb})} * 100\%$$

where $\Psi_{HbO2}$ represents the first calibration constant, $\Psi_{Hb}$ represents the second calibration constant, $A_{HbO2}$ represents a difference in attenuation of light signal attributable to oxyhemoglobin, and $A_{Hb}$ represents a difference in attenuation of light signal attributable to deoxyhemoglobin.

19. The method of claim 18, further comprising the steps of:
  determining a photon pathlength d*B; and
  determining the concentration of oxyhemoglobin and deoxyhemoglobin within the subject's tissue using the first and second calibration constants.

20. The method of claim 19, wherein the concentration of oxyhemoglobin and deoxyhemoglobin within the subject's tissue are determined using the equation $$\begin{bmatrix} A_{Hb} \\ A_{HbO_2} \end{bmatrix} (dB)^{-1} - \begin{bmatrix} \Psi_{Hb} \\ \Psi_{HbO_2} \end{bmatrix} (dB)^{-1} = \begin{bmatrix} Hb \\ HbO_2 \end{bmatrix}.$$

21. The method of claim 20, wherein the step of determining a difference in attenuation of the light signal between the first wavelength and the second wavelength utilizes the equation:

$$\Delta A_{\lambda 12} = \log[(I_{\lambda 2}/Io_{\lambda 2})*(I_{\lambda 1}/Io_{\lambda 1})] = \Delta \alpha_{c\lambda 12} cdB + \Delta G_{\lambda 12}$$

and the step of determining a difference in attenuation of the light signal between the first wavelength and the third wavelength utilizes the equation:

$$\Delta A_{\lambda 13}=\log[(I_{\lambda 3}/Io_{\lambda 3})*(I_{\lambda 1}/Io_{\lambda 1})]=\Delta \alpha_{c\lambda 13} cdB+\Delta G_{\lambda 13}.$$

22. The method of claim 20, wherein the step of determining a difference in attenuation of the light signal between the first wavelength and the second wavelength utilizes the equation:

$$\Delta A_{\lambda 12}=(\alpha'_{Hb\lambda 1}-\alpha'_{Hb\lambda 2})[Hb]dB+(\alpha'_{HbO_2\lambda 1}-\alpha'_{HbO_2\lambda 2})[HbO_2]dB+\Delta G_{\lambda 12}$$

and the step of determining a difference in attenuation of the light signal between the first wavelength and the third wavelength utilizes the equation:

$$\Delta A_{\lambda 13}=(\alpha'_{Hb\lambda 1}-\alpha'_{Hb\lambda 3})[Hb]dB+(\alpha'_{HbO_2\lambda 1}-\alpha'_{HbO_2\lambda 3})[HbO_2]dB+\Delta G_{\lambda 13}.$$

23. The method of claim 20, wherein the step of determining a difference in attenuation of the light signal between the first wavelength and the second wavelength utilizes the equation:

$$\Delta A_{\lambda 12}=(\alpha'_{Hb\lambda 1}-\alpha'_{Hb\lambda 2})[Hb]dB+(\alpha'_{HbO_2\lambda 1}-\alpha'_{HbO_2\lambda 2})[HbO_2]dB+\Delta G'_{\lambda 12}$$

and the step of determining a difference in attenuation of the light signal between the first wavelength and the third wavelength utilizes the equation:

$$\Delta A_{\lambda 13}=(\alpha'_{Hb\lambda 1}-\alpha'_{Hb\lambda 3})[Hb]dB+(\alpha'_{HbO_2\lambda 1}-\alpha'_{HbO_2\lambda 3})[HbO_2]dB+\Delta G'_{\lambda 13}.$$

24. The method of claim 14, wherein the step of determining the blood oxygen saturation level within the subject's tissue utilizes the equation:

$$CrSO_2 \% = \frac{(A_{HbO_2} - \Psi_{HbO_2})}{(A_{HbO_2} - \Psi_{HbO_2} + A_{Hb} - \Psi_{Hb})} * 100\%$$

where $\Psi_{HbO2}$ represents the first calibration constant, $\Psi_{Hb}$ represents the second calibration constant, $A_{HbO2}$ represents a difference in attenuation of light signal attributable to oxyhemoglobin, and $A_{Hb}$ represents a difference in attenuation of light signal attributable to deoxyhemoglobin.

25. The method of claim 24, further comprising the steps of:
   determining a photon pathlength d*B; and
   determining the concentration of oxyhemoglobin and deoxyhemoglobin within the subject's tissue using the first and second calibration constants.

26. The method of claim 25, wherein the concentration of oxyhemoglobin and deoxyhemoglobin within the subject's tissue are determined using the equation $$\begin{bmatrix} A_{Hb} \\ A_{HbO_2} \end{bmatrix}(dB)^{-1} - \begin{bmatrix} \Psi_{Hb} \\ \Psi_{HbO_2} \end{bmatrix}(dB)^{-1} = \begin{bmatrix} Hb \\ HbO_2 \end{bmatrix}.$$

27. The method of claim 26, wherein the step of determining a difference in attenuation of the light signal between the first wavelength and the second wavelength utilizes the equation:

$$\Delta A_{\lambda 12}=\log[(I_{\lambda 2}/Io_{\lambda 2})*(I_{\lambda 1}/Io_{\lambda 1})]=\Delta \alpha_{c\lambda 12} cdB+\Delta G_{\lambda 12}$$

and the step of determining a difference in attenuation of the light signal between the first wavelength and the third wavelength utilizes the equation:

$$\Delta A_{\lambda 13}=\log[(I_{\lambda 3}/Io_{\lambda 3})*(I_{\lambda 1}/Io_{\lambda 1})]=\Delta \alpha_{c\lambda 13} cdB+\Delta G_{\lambda 13}.$$

28. The method of claim 26, wherein the step of determining a difference in attenuation of the light signal between the first wavelength and the second wavelength utilizes the equation:

$$\Delta A_{\lambda 12}=(\alpha'_{Hb\lambda 1}-\alpha'_{Hb\lambda 2})[Hb]dB+(\alpha'_{HbO_2\lambda 1}-\alpha'_{HbO_2\lambda 2})[HbO_2]dB+\Delta G_{\lambda 12}$$

and the step of determining a difference in attenuation of the light signal between the first wavelength and the third wavelength utilizes the equation:

$$\Delta A_{\lambda 13}=(\alpha'_{Hb\lambda 1}-\alpha'_{Hb\lambda 3})[Hb]dB+(\alpha'_{HbO_2\lambda 1}-\alpha'_{HbO_2\lambda 3})[HbO_2]dB+\Delta G_{\lambda 13}.$$

29. The method of claim 26, wherein the step of determining a difference in attenuation of the light signal between the first wavelength and the second wavelength utilizes the equation:

$$\Delta A_{\lambda 12}=(\alpha'_{Hb\lambda 1}-\alpha'_{Hb\lambda 2})[Hb]dB+(\alpha'_{HbO_2\lambda 1}-\alpha'_{HbO_2\lambda 2})[HbO_2]dB+\Delta G'_{\lambda 12}$$

and the step of determining a difference in attenuation of the light signal between the first wavelength and the third wavelength utilizes the equation:

$$\Delta A_{\lambda 13}=(\alpha'_{Hb\lambda 1}-\alpha'_{Hb\lambda 3})[Hb]dB+(\alpha'_{HbO_2\lambda 1}-\alpha'_{HbO_2\lambda 3})[HbO_2]dB+\Delta G'_{\lambda 13}.$$

30. A method for calibrating a near infrared spectrophotometric sensor for use in determining the blood oxygen saturation level within a subject's tissue, said method comprising the steps of:
   transmitting a light signal into the subject's tissue at a predetermined first intensity, wherein the transmitted light signal includes a first wavelength, a second wavelength, and a third wavelength;
   sensing a second intensity of the light signal along the first, second, and third wavelengths after the light signal travels through the subject;
   determining an attenuation of the light signal for each of the first, second, and third wavelengths using the predetermined first intensity and the sensed second intensity of the first, second, and third wavelengths;
   determining a difference in attenuation of the light signal between the first wavelength and the second wavelength, and between the first wavelength and the third wavelength;
   determining a first calibration constant and a second calibration constant using empirical data developed from the subject at or about the same time as when the sensing occurs; and
   calibrating the sensor using the first calibration constant and the second calibration constant.

31. The method of claim 30, wherein the empirical data is collected by discretely sampling a venous blood source and an arterial blood source from the subject.

32. The method of claim 30, wherein the empirical data is collected by continuously monitoring a venous blood source and an arterial blood source from the subject.

33. The method of claim 30, wherein the sensor is calibrated using equation:

$$SmvO_2 = Kv*SvO_2 + Ka*SaO_2.$$

34. The method of claim 33, wherein the step of determining a difference in attenuation of the light signal between the first wavelength and the second wavelength utilizes the equation:

$$\Delta A_{\lambda 12} = \log[(I_{\lambda 2}/Io_{\lambda 2})*(I_{\lambda 1}/Io_{\lambda 1})] = \Delta \alpha_{c\lambda 12} cdB + \Delta G_{\lambda 12}$$

and the step of determining a difference in attenuation of the light signal between the first wavelength and the third wavelength utilizes the equation:

$$\Delta A_{\lambda 13} = \log[(I_{\lambda 3}/Io_{\lambda 3})*(I_{\lambda 1}/Io_{\lambda 1})] = \Delta \alpha_{c\lambda 13} cdB + \Delta G_{\lambda 13}.$$

35. The method of claim 33, wherein the step of determining a difference in attenuation of the light signal between the first wavelength and the second wavelength utilizes the equation:

$$\Delta A_{\lambda 12} = (\alpha'_{Hb\lambda 1} - \alpha'_{Hb\lambda 2})[Hb]dB + (\alpha'_{HbO_2\lambda 1} - \alpha'_{HbO_2\lambda 2})[HbO_2]dB + \Delta G_{\lambda 12}$$

and the step of determining a difference in attenuation of the light signal between the first wavelength and the third wavelength utilizes the equation:

$$\Delta A_{\lambda 13} = (\alpha'_{Hb\lambda 1} - \alpha'_{Hb\lambda 3})[Hb]dB + (\alpha'_{HbO_2\lambda 1} - \alpha'_{HbO_2\lambda 3})[HbO_2]dB + \Delta G_{\lambda 13}.$$

36. The method of claim 33, wherein the step of determining a difference in attenuation of the light signal between the first wavelength and the second wavelength utilizes the equation:

$$\Delta A_{\lambda 12} = (\alpha'_{Hb\lambda 1} - \alpha'_{Hb\lambda 2})[Hb]dB + (\alpha'_{HbO_2\lambda 1} - \alpha'_{HbO_2\lambda 2})[HbO_2]dB + \Delta G'_{\lambda 12}$$

and the step of determining a difference in attenuation of the light signal between the first wavelength and the third wavelength utilizes the equation:

$$\Delta A_{\lambda 13} = (\alpha'_{Hb\lambda 1} - \alpha'_{Hb\lambda 3})[Hb]dB + (\alpha'_{HbO_2\lambda 1} - \alpha'_{HbO_2\lambda 3})[HbO_2]dB + \Delta G'_{\lambda 13}.$$

37. A method for calibrating a NIRS sensor, said method comprising the steps of:
transmitting a light signal from a calibrated NIRS sensor into a reference sample at a predetermined first intensity, wherein the transmitted light signal includes a first wavelength, a second wavelength, and a third wavelength;
sensing a second intensity of the light signal with the calibrated NIRS sensor along the first, second, and third wavelengths after the light signal travels through the reference sample;
determining a first attenuation of the light signal for each of the first, second, and third wavelengths using the predetermined first intensity and the second intensity of the light signal sensed with the calibrated NIRS sensor;
transmitting a light signal from an uncalibrated second NIRS sensor into the reference sample at the predetermined first intensity, wherein the transmitted light signal includes a first wavelength, a second wavelength, and a third wavelength;
sensing a second intensity of the light signal with the uncalibrated second NIRS sensor along the first, second, and third wavelengths after the light signal travels through the subject;
determining a second attenuation of the light signal for each of the first, second, and third wavelengths using the predetermined first intensity and the second intensity of the first, second, and third wavelengths sensed with the uncalibrated second NIRS sensor;
adjusting the uncalibrated second NIRS sensor so that the second attenuation substantially agrees with the first attenuation.

38. A method for determining a blood oxygen saturation level within a subject's tissue attributable to venous blood, said method comprising the steps of:
providing a NIRS sensor for sensing the subject's tissue;
determining a blood oxygen saturation level with the subject's tissue using the NIRS sensor:
determining a blood oxygen saturation level attributable to arterial blood within the subject's tissue using a pulse oximetry technique; and
determining a blood oxygen saturation level attributable to venous blood within the subject's tissue using the equation:

$$SvO_2 = \frac{CrSO_2 - (Ka*SpO_2)}{Kv}.$$

39. The method of claim 38, wherein the blood oxygen saturation level with the subject's tissue is determined using the following steps:
transmitting a light signal into the subject's tissue at a predetermined first intensity, wherein the transmitted light signal includes a first wavelength, a second wavelength, and a third wavelength;
sensing a second intensity of the light signal along the first, second, and third wavelengths after the light signal travels through the subject;
determining an attenuation of the light signal for each of the first, second, and third wavelengths using the predetermined first intensity and the sensed second intensity of the first, second, and third wavelengths;
determining a difference in attenuation of the light signal between the first wavelength and the second wavelength, and between the first wavelength and the third wavelength;
determining a first calibration constant and a second calibration constant using empirical data developed from the subject at or about the same time as when the sensing occurs;
determining the blood oxygen saturation level within the subject's tissue using the difference in attenuation between the first wavelength and the second wavelength, and the difference in attenuation between the first wavelength and the third wavelength.

40. A method for non-invasively determining a concentration of oxyhemoglobin and a concentration of deoxyhemoglobin within a subject's tissue using a near infrared spectrophotometric sensor, said method comprising the steps of:
(a) determining a blood oxygen saturation level with the subject's tissue by
transmitting a light signal into the subject's tissue from a NIRS sensor at a predetermined first intensity, wherein the transmitted light signal includes a first wavelength, a second wavelength, and a third wavelength;
sensing a second intensity of the light signal along the first, second, and third wavelengths after the light signal travels through the subject using the sensor;
wherein the sensor is calibrated using empirical data that relates to the subject's tissue that is sensed by the sensor to account for light signal attenuation resulting from light signal scattering within the subject's tissue;
determining an attenuation of the light signal for each of the first, second, and third wavelengths using the predetermined first intensity and the sensed second intensity of the first, second, and third wavelengths;
determining a difference in attenuation of the light signal between the first wavelength and the second wavelength, and between the first wavelength and the third wavelength;
determining a first calibration constant and a second calibration constant using empirical data developed from the subject at or about the same time as when the sensing occurs;
determining the blood oxygen saturation level within the subject's tissue using the difference in attenuation between the first wavelength and the second wavelength, and the difference in attenuation between the first wavelength and the third wavelength, and the first calibration constant and the second calibration constant;
(b) determining a photon pathlength d*B; and
(c) determining the concentration of oxyhemoglobin and the concentration of deoxyhemoglobin within the subject's tissue using the first and second calibration constants.

41. The method of claim 40, wherein the concentration of oxyhemoglobin and the concentration of deoxyhemoglobin within the subject's tissue are determined using the equation:

$$\begin{bmatrix} A_{Hb} \\ A_{HbO_2} \end{bmatrix}(dB)^{-1} - \begin{bmatrix} \Psi_{Hb} \\ \Psi_{HbO_2} \end{bmatrix}(dB)^{-1} = \begin{bmatrix} Hb \\ HbO_2 \end{bmatrix}$$

where $\Psi_{HbO2}$ represents the first calibration constant, $\Psi_{Hb}$ represents the second calibration constant, $A_{HbO2}$ represents a difference in attenuation of light signal attributable to oxyhemoglobin, and $A_{Hb}$ represents a difference in attenuation of light signal attributable to deoxyhemoglobin.

42. A method for non-invasively determining a concentration of oxyhemoglobin and a concentration of deoxyhemoglobin within a subject's tissue at an initial time t1 and a subsequent time t2 using a near infrared spectrophotometric sensor, said method comprising the steps of:
(a) determining a blood oxygen saturation level with the subject's tissue by
transmitting a light signal into the subject's tissue from a NIRS sensor at a predetermined first intensity, wherein the transmitted light signal includes a first wavelength, a second wavelength, and a third wavelength;
sensing a second intensity of the light signal along the first, second, and third wavelengths after the light signal travels through the subject using the sensor;
wherein the sensor is calibrated using empirical data that relates to the subject's tissue that is sensed by the sensor to account for light signal attenuation resulting from light signal scattering within the subject's tissue;
determining an attenuation of the light signal for each of the first, second, and third wavelengths using the predetermined first intensity and the sensed second intensity of the first, second, and third wavelengths;
determining a difference in attenuation of the light signal between the first wavelength and the second wavelength, and between the first wavelength and the third wavelength;
determining a first calibration constant and a second calibration constant using empirical data developed from the subject at or about the same time as when the sensing occurs;
determining the blood oxygen saturation level within the subject's tissue using the difference in attenuation between the first wavelength and the second wavelength, and the difference in attenuation between the first wavelength and the third wavelength, and the first calibration constant and the second calibration constant;
(b) determining a photon pathlength d*B;
(c) determining the concentration of oxyhemoglobin and the concentration of deoxyhemoglobin within the subject's tissue at the initial time t1 using the equation:

$$\begin{bmatrix} A_{Hb} \\ A_{HbO_2} \end{bmatrix}(dB)^{-1} - \begin{bmatrix} \Psi_{Hb} \\ \Psi_{HbO_2} \end{bmatrix}(dB)^{-1} = \begin{bmatrix} Hb \\ HbO_2 \end{bmatrix}_{t1}$$

where $\Psi_{HbO2}$ represents the first calibration constant, $\Psi_{Hb}$ represents the second calibration constant, $A_{HbO2}$ represents a difference in attenuation of light signal attributable to oxyhemoglobin, and $A_{Hb}$ represents a difference in attenuation of light signal attributable to deoxyhemoglobin; and
(d) determining a change in the concentration of oxyhemoglobin and a change in the concentration of deoxyhemoglobin from the initial time t1 to a subsequent second time t2 are determined using the equation:

$$\begin{bmatrix} -\log(I_{t2}/I_{t1})_{\lambda 1}/(d*B_{\lambda 1}) \\ -\log(I_{t2}/I_{t1})_{\lambda 2}/(d*B_{\lambda 2}) \\ -\log(I_{t2}/I_{t1})_{\lambda 3}/(d*B_{\lambda 3}) \end{bmatrix} = \begin{bmatrix} \alpha_{Hb\lambda 1} & \alpha_{HbO_2\lambda 1} \\ \alpha_{Hb\lambda 2} & \alpha_{HbO_2\lambda 2} \\ \alpha_{Hb\lambda 3} & \alpha_{HbO_2\lambda 3} \end{bmatrix} * \begin{bmatrix} \Delta Hb \\ \Delta HbO_2 \end{bmatrix};$$

and
(e) determining the concentration of oxyhemoglobin and the concentration of deoxyhemoglobin within the subject's tissue at the subsequent time t2 using the equations:

$$[Hb]_{t2} = \Delta Hb(t_2) + [Hb]_{t1}$$

and $$[HbO_2]_{t2} = \Delta HbO_2(t_2) + [HbO_2]_{t1}.$$

43. A method for non-invasively determining a blood oxygen saturation level within a subject's tissue using a near infrared spectrophotometric sensor, said method comprising the steps of:

transmitting a light signal into the subject's tissue at a predetermined first intensity using the sensor;

sensing a second intensity of the light signal along three or more selectively chosen wavelengths after the light signal travels through the subject using the sensor;

wherein the sensor is calibrated using empirical data that relates to the subject's tissue that is sensed by the sensor to account for light signal attenuation resulting from light signal scattering within the subject's tissue;

determining an attenuation of the light signal for at least "n" number of the selectively chosen wavelengths using the predetermined first intensity and the sensed second intensity of the selectively chosen wavelengths, where "n" is an integer equal to or greater than three;

determining a difference in attenuation of the light signal between a first wavelength and each of "n" number of the selectively chosen wavelengths;

determining the blood oxygen saturation level within the subject's tissue using the difference in attenuation between the first wavelength and each of the "n" number of other selectively chosen wavelengths.

44. A method for determining a blood oxygen saturation level within a subject's tissue using a near infrared spectrophotometric sensor attached to the skin of the subject, said method comprising the steps of:

transmitting a light signal into the subject's tissue at a predetermined first intensity;

sensing a second intensity of the light signal along three or more selectively chosen wavelengths after the light signal travels through the subject;

determining an attenuation of the light signal for at least "n" number of the selectively chosen wavelengths using the predetermined first intensity and the sensed second intensity of the selectively chosen wavelengths, where "n" is an integer equal to or greater than three;

determining a difference in attenuation of the light signal between a first wavelength and each of "n" number of the selectively chosen wavelengths;

determining a first calibration constant and a second calibration constant using empirical data developed from the subject at or about the same time as when the sensing occurs;

determining the blood oxygen saturation level within the subject's tissue using the difference in attenuation between the first wavelength and each of "n" number of the selectively chosen wavelengths, and the first calibration constant and the second calibration constant.

* * * * *

UNITED STATES PATENT AND TRADEMARK OFFICE
CERTIFICATE OF CORRECTION

PATENT NO.    : 6,456,862 B2
DATED         : September 24, 2002
INVENTOR(S)   : Paul B. Benni It is certified that error appears in the above-identified patent and that said Letters Patent is hereby corrected as shown below:

Signed and Sealed this

Eighteenth Day of February, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,456,862 B2
DATED : September 24, 2002
INVENTOR(S) : Paul B. Benni It is certified that error appears in the above-identified patent and that said Letters Patent is hereby corrected as shown below:

Column 6,
Line 65, the equation should read:

$$\Delta A_{\lambda 12} = \log\left[(I_{\lambda 2}/Io_{\lambda 2})/(I_{\lambda 1}/Io_{\lambda 1})\right] = \Delta\alpha_{c\lambda 12}cdB + \Delta G_{\lambda 12}$$

Column 7,
Line 8, the equation should read: $B_\lambda = B * k_\lambda$

Line 24, the equation should read:

$$\Delta A_{\lambda 12} = (\alpha'_{Hb\lambda 1} - \alpha'_{Hb\lambda 2})[Hb]dB + (\alpha'_{HbO_2,\lambda 1} - \alpha'_{HbO_2,\lambda 2})[HbO_2]dB + \Delta G_{\lambda 12}$$

Column 12,
Claim 7, the first equation should read:

$$\Delta A_{\lambda 12} = \log\left[(I_{\lambda 2}/Io_{\lambda 2})/(I_{\lambda 1}/Io_{\lambda 1})\right] = \Delta\alpha_{c\lambda 12}cdB + \Delta G_{\lambda 12}$$

and the second equation should read:

$$\Delta A_{\lambda 13} = \log\left[(I_{\lambda 3}/Io_{\lambda 3})/(I_{\lambda 1}/Io_{\lambda 1})\right] = \Delta\alpha_{c\lambda 13}cdB + \Delta G_{\lambda 13}$$

Column 13,
Claim 10, the first equation should read:

$$\Delta A_{\lambda 12} = \log\left[(I_{\lambda 2}/Io_{\lambda 2})/(I_{\lambda 1}/Io_{\lambda 1})\right] = \Delta\alpha_{c\lambda 12}cdB + \Delta G_{\lambda 12}$$

and the second equation should read:

$$\Delta A_{\lambda 13} = \log\left[(I_{\lambda 3}/Io_{\lambda 3})/(I_{\lambda 1}/Io_{\lambda 1})\right] = \Delta\alpha_{c\lambda 13}cdB + \Delta G_{\lambda 13}$$

Column 14,
Claim 21, the first equation should read:

$$\Delta A_{\lambda 12} = \log\left[(I_{\lambda 2}/Io_{\lambda 2})/(I_{\lambda 1}/Io_{\lambda 1})\right] = \Delta\alpha_{c\lambda 12}cdB + \Delta G_{\lambda 12}$$

and the second equation should read:

$$\Delta A_{\lambda 13} = \log\left[(I_{\lambda 3}/Io_{\lambda 3})/(I_{\lambda 1}/Io_{\lambda 1})\right] = \Delta\alpha_{c\lambda 13}cdB + \Delta G_{\lambda 13}$$

UNITED STATES PATENT AND TRADEMARK OFFICE
CERTIFICATE OF CORRECTION

PATENT NO.   : 6,456,862 B2
DATED        : September 24, 2002
INVENTOR(S)  : Paul B. Benni It is certified that error appears in the above-identified patent and that said Letters Patent is hereby corrected as shown below:

Column 16,
Claim 27, the first equation should read:

$$\Delta A_{\lambda 12} = \log\left[\left(I_{\lambda 2}/Io_{\lambda 2}\right)/\left(I_{\lambda 1}/Io_{\lambda 1}\right)\right] = \Delta\alpha_{c\lambda 12} cdB + \Delta G_{\lambda 12}$$

and the second equation should read:

$$\Delta A_{\lambda 13} = \log\left[\left(I_{\lambda 3}/Io_{\lambda 3}\right)/\left(I_{\lambda 1}/Io_{\lambda 1}\right)\right] = \Delta\alpha_{c\lambda 13} cdB + \Delta G_{\lambda 13}$$

Column 17,
Claim 34, the first equation should read:

$$\Delta A_{\lambda 12} = \log\left[\left(I_{\lambda 2}/Io_{\lambda 2}\right)/\left(I_{\lambda 1}/Io_{\lambda 1}\right)\right] = \Delta\alpha_{c\lambda 12} cdB + \Delta G_{\lambda 12}$$

and the second equation should read:

$$\Delta A_{\lambda 13} = \log\left[\left(I_{\lambda 3}/Io_{\lambda 3}\right)/\left(I_{\lambda 1}/Io_{\lambda 1}\right)\right] = \Delta\alpha_{c\lambda 13} cdB + \Delta G_{\lambda 13}$$

Signed and Sealed this

Twenty-fifth Day of February, 2003

JAMES E. ROGAN
*Director of the United States Patent and Trademark Office*